United States Patent [19]

Whyman

[11] 4,331,825

[45] May 25, 1982

[54] PRODUCTION OF METHANE BY HYDROGENOLYSIS OF HYDROCARBONS AND RUTHENIUM CATALYSTS THEREFOR

[75] Inventor: Robin Whyman, Christleton, England

[73] Assignee: Imperial Chemical Industries Limited, London, England

[21] Appl. No.: 93,494

[22] Filed: Nov. 13, 1979

[30] Foreign Application Priority Data

Nov. 16, 1978 [GB] United Kingdom ............... 44764/78

[51] Int. Cl.$^3$ .............................................. C07C 4/02
[52] U.S. Cl. .................................. 585/752; 208/139; 585/489
[58] Field of Search ................. 208/139; 585/752, 489

[56] References Cited

U.S. PATENT DOCUMENTS

| | | | |
|---|---|---|---|
| 3,180,902 | 4/1965 | Andersen et al. | 585/752 |
| 3,966,833 | 6/1976 | Cosyns et al. | 585/489 |
| 4,065,514 | 12/1977 | Bartley | 208/111 |
| 4,152,247 | 5/1979 | Antos | 208/139 |
| 4,177,219 | 12/1979 | Feinstein et al. | 585/489 |
| 4,183,804 | 1/1980 | Antos | 208/139 |

OTHER PUBLICATIONS

Kikuchi et al., J. Catalysis, 22 226–236 (1971).
Carter et al., J. Catalysis, 20 223–229 (1971).
Kempling et al., Ind. Eng. Chem. Process Res & Dev., 9, Jan. 1970.
Ragaini et al., Reaction Kinetics & Catalysis Letters, 2 19–27 (1975).

*Primary Examiner*—Curtis R. Davis
*Attorney, Agent, or Firm*—Cushman, Darby & Cushman

[57] ABSTRACT

Supported ruthenium metal catalysts prepared by reduction of carbonyl compounds give improved yields of methane in the hydro-cracking of hydrocarbons, especially alkanes and alkyl aromatics. Alkanes may be cracked to methane at low temperature (200°–300° C.) and the de-alkylation of alkyl benzenes may be controlled sufficiently to allow removal of isomers e.g. ethylbenzene from xylenes. The novel catalysts comprise ruthenium clusters having average dimensions below 20 Å.

17 Claims, No Drawings

PRODUCTION OF METHANE BY HYDROGENOLYSIS OF HYDROCARBONS AND RUTHENIUM CATALYSTS THEREFOR

This invention relates to a chemical process for the production of methane by the hydro-cracking of hydrocarbons.

According to the present invention we provide a process for the production of methane from an organic hydrocarbon containing a plurality of carbon atoms, a process wherein the organic compound is contacted in the presence of hydrogen with a supported ruthenium catalyst prepared by a process comprising the de-carbonylation of a ruthenium carbonyl compound.

The de-carbonylation of the ruthenium carbonyl compound may be a partial de-carbonylation but substantially complete removal of carbonyl groups is preferred. The decarbonylation is preferably conducted by thermal decomposition for example either under vacuum or in the presence of hydrogen but other suitable methods of decarbonylation may be employed.

The support on which the ruthenium catalyst is carried may be selected from conventional catalyst supports, for example particulate oxides or salts, zeolites and especially silica. The particle size of the support is not thought to be critical to the behaviour of the catalyst, but we have observed that support materials having particle sizes in the range 50–300 $\mu$m, preferably 75–150 $\mu$m are most convenient.

Conversely the size of the ruthenium catalyst particles which when small are often referred to as metal clusters, is important in the use of the catalyst because the activity and/or the selectivity of the hydrogenolysis reaction may be affected thereby. When ruthenium carbonyl compounds are de-carbonylated by a process of heating, preferably in a stream of hydrogen and nitrogen gases to a temperature of up to 500° C., metal clusters are produced, for example, small particles having an average dimension in the range 10–20 Å (i.e. 1–2 nm). According to our measurements of particle sizes these are smaller clusters than are conventionally produced from other ruthenium compounds for example, from the trichloride where particles having an average size in the range of 30–50 Å are observed on reduction.

The ruthenium carbonyl compound from which the catalyst is prepared for the process of this invention is a compound containing a carbonyl ligand co-ordinated to a ruthenium atom and may include other groups or ligands (e.g. hydrogen or carbon) and also metal nuclei in addition to the ruthenium nucleus. However, we have found that the use of compounds containing nuclei of the metal ruthenium only are very suitable and especially compounds containing a plurality of ruthenium atoms, preferably at least three atoms joined by metal-metal bonds e.g. the polynuclear ruthenium carbonyl compounds $Ru_3(CO)_{12}$ and $Ru_6(CO)_{17}C$.

Other compounds which may be used include the hydrido carbonyls $H_4Ru_4(CO)_{12}$; $H_2Ru_4(CO)_{13}$ and $[HRu_3(CO)_{12}]^+$ or carbide carbonyls e.g. $[Ru_6(CO)_{16}C]^{2-}$ in which the ruthenium may be present in complex anions or cations.

For the production of the supported catalyst we prefer to deposit the ruthenium carbonyl compound from solution onto the support material (e.g. by evaporation of solvent) care being taken to exclude moisture and usually oxygen, conveniently by evaporating under dry nitrogen. For best results it is preferable to remove any inhomogeneities in the deposited carbonyl compound dispersed over the surface of the support. This may be done conveniently by applying to the supported carbonyl compound dry solvent, which is then evaporated whilst the supported compound is stirred. The ruthenium carbonyl is suitably decomposed by the application of heat for example by heating to a temperature in the range 100° C. to 500° C., more suitably up to 350° C. and preferably in a nitrogen/hydrogen atmosphere. It is especially beneficial to heat the carbonyl compound in two stages suitably the first at 100°–200° C. under nitrogen only and the second stage at a higher temperature for example from 300°–350° C. under a nitrogen/hydrogen atmosphere preferably containing from 10% to 50% by volume of hydrogen. From a procedure as outlined above a catalyst is prepared which when examined by electron microscopy may be shown to comprise small particles (i.e. clusters) of ruthenium on the support; particles which have an average size within the range 10–20 Å (1–2 nm).

The ruthenium catalysts which are described hereinbefore are advantageous when used in hydrogenolysis reactions of hydrocarbons (particularly compounds containing alkyl groups) because high yields of methane may be produced selectively thereby at relatively low temperatures.

The process wherein the hydrocarbon is contacted with the ruthenium catalyst should be preferably in the absence of oxygen and is preferably conducted in such a way that hydrogen gas is present with the hydrocarbon when it contacts the catalyst. The temperature of the system at the region of contact may be suitably from 100°–500° C., preferably from 200°–300° C., because the catalyst system used in this invention is found to be especially active in producing methane by lower temperature hydro-cracking of alkanes and alkyl aromatic compounds e.g. ethyl benzene. Other catalysts are known to be selective in the production of methane from the cracking of alkanes but at temperatures of greater than 350° C. which obviously requires a much greater expenditure of energy to maintain the reaction over long periods of time. Moreover the life of materials of construction is greater for a continuous process operated at a lower temperature. The yields of methane from the process of this invention are typically greater than 90% expressed as the proportion of methane in the total hydrocarbon product.

The organic hydrocarbon compound is preferably an aliphatic compound or aromatic compound containing at least one alkyl group. We especially prefer to use alkanes (e.g. up to $C_{14}$) or alkyl benzenes and an alkane feed stock may be conveniently a pure, branched or straight alkane (for example normal heptane) or it may be a mixture of alkanes for example, paraffin cuts from petroleum refineries containing for example, alkanes from $C_7$ to $C_{14}$. Hydrocarbon compounds not containing alkyl groups (e.g. fused aromatic ring compounds) may be used and therefore coal, coke and hydrocarbon extracts from these materials represent a useful feed-stock but in general higher temperatures are necessary for the selective production of methane e.g. temperatures from 300°–500° C.

The hydrocarbon (e.g. alkane mixture) may be mixed in vapour form with both hydrogen and an inert gas (e.g. nitrogen) usually prior to contact with the catalyst and the mixture of gases passed over the supported catalyst conveniently contained in a tubular reactor. The volume proportion of the hydrocarbon to hydrogen in the feed to the catalyst is preferably in the range from 1:2 to 1:25 the middle region ca. 1:10 being very suitable, depending on the nature of the feed. The other component of the mixture, the inert gas or gases, may be present in preferred proportions relative to the hydrogen which may range from 25:1 to 5:1.

Thus the process of this invention may be used advantageously to produce methane from a large range of aliphatic hydrocarbons at lower temperatures and at higher conversions than previously possible. For example naphtha may be reduced to methane as a precursor to a steam-reforming process.

With alkylaromatic compounds, in addition to the total conversion to methane at high temperatures, this invention gives rise to the ability to control the selectivity of the reaction at lower temperatures. A controlled dealkylation may be effected which produces various aromatic compounds in addition to methane. For example with ethylbenzene as feedstock the reaction conditions may be arranged to produce a mixture of either toluene and methane (1:1). Further, it is an important facet of this process that the above selectivity can be applied to mixtures of alkyl aromatic compounds such that one component may be dealkylated whilst leaving others largely unchanged. For example conditions may be arranged in the treatment of ethylbenzene and xylenes with hydrogen to convert ethylbenzene to toluene and methane without significant loss of xylenes. Such a process can with advantage be used to remove ethylbenzene from mixed xylenes without the need for a distillation stage. The process may be utilised either as precursor to or preferably in combination with a xylene isomerisation catalyst.

The invention is illustrated by the following examples.

EXAMPLE 1

The catalyst composition was prepared by the addition of 5 gm Grace Davison 952 silica (pre-dried either by degassing at $10^{-3}$ mm and 550° C. for 4 hours or by treatment with air at 550° C. for 4 hours) to a stirred solution of tri-ruthenium dodecarbonyl (0.11 gm) in dry toluene (150 cm$^3$). The solvent was slowly removed by evaporation under a stream of dry nitrogen to give a yellow free-flowing powder. Any inhomogenities in the colour of the powder, e.g. local orange concentrations due to unsupported crystalline $Ru_3(CO)_{12}$, were removed by the addition of further dry toluene and subsequent evaporation with stirring.

The pale yellow powder was transferred to a tubular reactor and the ruthenium carbonyl decomposed by heating to 120°–150° C. under a flow of nitrogen followed by a 4:1 by volume nitrogen:hydrogen mixture at 350° C. for 4 hours.

The resulting light grey powder contained ca. 1% ruthenium metal evenly distributed throughout the silica as fairly uniformly sized particles having dimensions of 15–20 Å as measured by electron microscopy.

The concentration of metal on the support may be varied as described by using the appropriate proportions of tri-ruthenium dodecacarbonyl.

A stream of nitrogen was metered through a bubbler containing n-heptane and combined with a stream of hydrogen to give a nitrogen:hydrogen:heptane volume ratio of 100:10:1. This mixture was passed through a tubular reactor of ¼" diameter containing 2.5 g of 1% ruthenium on silica, prepared using the procedure described before in this Example, deposited on a sintered glass frit. The temperature of the reactor was increased from 100° C. at 50° C. intervals and the resultant gaseous products analysed by gas chromatography to give the results listed in Table I.

TABLE I

| Catalytic hydrogenolysis of n-heptane | | |
|---|---|---|
| Catalyst: | 2.5g of 1% ruthenium on silica | |
| Pressure: | 0 p.s.i. g | |
| Liquid Hourly Space velocity: | 0.3 vol substrate/vol catalyst/hr | |
| Temp (°C.) | Heptane Conversion (%) | Products |
| 100 | <1 | |
| 150 | 7 | |
| 200 | 87 | $CH_4 + C_2H_6$ |
| 250 | 100 | $CH_4$ |

From the data in Table I it is evident that the ruthenium catalyst is very active for the hydrogenolysis of n-heptane to methane at relatively low temperatures i.e. between 200°–300° C.

EXAMPLE 2

Using the procedure described in Example 1 the activities of catalysts derived from polynuclear ruthenium carbonyls were compared with those of silica-supported ruthenium catalysts prepared by conventional methods e.g. metal chloride impregnation and ion-exchange. The results of these experiments obtained at 250° C. are listed in Table II.

TABLE II

| Hydrogenolysis of n-heptane with silica-supported ruthenium catalysts | | | | |
|---|---|---|---|---|
| Pressure: | 0 p.s.i. g | | | |
| Temperature: | 250° C. | | | |
| $H_2/C_7$ ratio: | 10/1 by volume | | | |
| Liquid Hourly Space Velocity: | 0.3 vol substrate/vol catalyst/hour | | | |
| Catalyst Precursor | Metal (%) | Particle size (A) | Heptane Conversion (%) | % methane in Products (%) Selectivity |
| A $Ru_3(CO)_{12}$ | 1.7 | 15–20 | 100 | 100 |
| B $Ru_6C(CO)_{17}$ | 1.4 | 15–20 | 96 | 90 |
| C $[Ru(NH_3)_5N_2]Cl_2$ | 2.3 | 25–30 | 26 | 65 |
| D $RuCl_3\ 3H_2O$ | 0.5 | 35–45 | 18 | 65 |

From the data in Table II it is evident that the ruthenium carbonyl derived catalysts (A, B) show very significantly enhanced hydrogenolysis activity over the conventionally prepared catalysts (C, D)
Particle size quoted is the peak of the distribution of particle sizes in the samples measured.

EXAMPLE 3

The procedure described in Example 1 was used to prepare a ruthenium catalyst supported on γ-alumina. This material was tested as a catalyst for the hydrogenolysis of n-heptane and give the results listed in Table III.

TABLE III

| Hydrogenolysis of n-heptane with alumina-supported ruthenium catalysts | | | | | | | |
|---|---|---|---|---|---|---|---|
| Catalyst: | 2.0 gm of 0.9% ruthenium on γ-alumina | | | | | | |
| Pressure: | 0 p.s.i. g | | | | | | |
| Temperature: | 325° C. | | | | | | |
| $H_2/C_7$ ratio: | 10/1 by volume | | | | | | |
| LHSV: | 0.3 vol/vol/hour | | | | | | |
| Catalyst Precursor | Heptane Conversion (%) | Products (%) Selectivity | | | | | |
| | | $C_1$ | $C_2$ | $C_3$ | $C_4$ | $C_5$ | $C_6$ |
| $Ru_3(CO)_{12}$ | 25.5 | 71.6 | 12.6 | 5.2 | 3.3 | 3.2 | 4.0 |

EXAMPLE 4

When n-dodecane instead of n-heptane was passed over the catalyst using the procedure described in Example 1 the results listed in Table IV were obtained.

TABLE IV

Catalytic hydrogenolysis of n-dodecane

| Catalyst: | 1.0 g of 2.2% ruthenium on silica |
| --- | --- |
| Pressure: | 0 p.s.i. g |
| $H_2/C_{12}$ ratio: | 10/1 by volume |
| LHSV: | ca 0.1 vol/vol/hour |

| Temp (°C.) | Dodecane Conversion (%) | Product Selectivity (%) | | | |
| --- | --- | --- | --- | --- | --- |
| | | $C_1$ | $C_2$ | $C_6$ | $C_8$ |
| 175 | 1.0 | | | | |
| 200 | 23.7 | 81.4 | 7.25 | 4.03 | 7.25 |
| 225 | 40.0 | 91.4 | 2.39 | 3.34 | 2.87 |
| 250 | 39.0 | 100 | | | |
| 275 | 39.0 | 100 | | | |

Since the stoichiometry for complete conversion of n-dodecane into methane requires an $H_2/C_{12}$ ratio of 11:1 the maximum conversion attainable under the above reaction conditions is only 90%.

EXAMPLE 5

When ethylbenzene instead of n-heptane was passed over the silica-supported catalyst, using the procedure described in Example 1, the results listed in Table V were obtained.

TABLE V

Catalytic hydrogenolysis of ethylbenzene

| Catalyst: | 1.0 gm of 2.9% Ru on silica |
| --- | --- |
| Pressure: | 0 p.s.i. g |
| $H_2/EB$ ratio: | 10:1 by volume |
| LHSV: | 0.1 vol/vol/hour |

| Temp °C. | EB % conversion | Products % Selectivity | | | | |
| --- | --- | --- | --- | --- | --- | --- |
| | | Methane | Ethane | Benzene | Toluene | Ethylcyclohexane |
| 200 | 16.0 | 45.2 | 1.5 | — | 35.4 | 15.0 |
| 225 | 30.0 | 52.9 | 1.7 | 0.7 | 41.0 | — |
| 250 | 30.7 | 64.8 | 2.4 | 1.8 | 31.0 | — |
| 275 | 28.3 | 71.0 | 1.8 | 1.8 | 26.0 | — |
| 300 | 41.0 | 87.0 | 1.1 | 1.5 | 10.5 | — |
| 325 | 52.7 | 92.0 | 0.5 | 1.1 | 6.4 | — |

From the results in Table V it is evident that, with appropriate choice of reaction conditions, the ruthenium catalyst may be used for the highly selective hydrogenolysis of ethylbenzene to toluene and methane and, at higher temperature, for the destructive hydrogenation of aromatic rings to give high yields of methane.

EXAMPLE 6

When a mixture of ethylbenzene, ortho-xylene and paraxylene was passed over a silica-supported ruthenium catalyst, using the procedure described in Example 1, the results listed in Table VI were obtained.

TABLE VI

Catalytic hydrogenolysis of ethylbenzene, ortho- and para-xylenes

| Catalyst: | 1.0 gm of 2.5% Ru on silica |
| --- | --- |
| Pressure: | 0 p.s.i. g |
| Ethylbenzene:p-xylene:o-xylene: | 2.2:2.0:1.0 |
| $H_2$/hydrocarbon: | 10/1 by volume |
| LHSV: | 0.1 vol (total substrate)/vol catalyst/hour |

| Temp °C. | Conversion (%) | | | Product Selectivity (%) | | | |
| --- | --- | --- | --- | --- | --- | --- | --- |
| | Ethylbenzene | p-Xylene | o-Xylene | Methane | Ethane | Benzene | Toluene |
| 200 | 21.0 | 5.0 | 0 | 65.2 | 0 | 0 | 34.8 |
| 225 | 23.0 | 5.5 | 0 | 68.3 | 0 | 0 | 31.7 |
| 250 | 26.5 | 17.5 | 8.0 | 79.9 | 2.2 | 1.4 | 16.4 |
| 275 | 34.0 | 22.2 | 14.3 | 89.8 | 0 | 1.0 | 10.2 |
| 300 | 39.6 | 26.0 | 16.8 | 93.3 | 0 | 0.5 | 6.2 |

EXAMPLE 7

A mixture of 2.0 g anthracene and 0.85 g of a silica-supported ruthenium catalyst (prepared using the procedure described in Example 1—ruthenium content 2.1%) contained in a glass liner was transferred to a stainless steel autoclave of 150 ml capacity. After flushing with nitrogen the autoclave was pressurised with hydrogen and heated to 250° C. for 4 hours, the pressure being adjusted to 1500 psig at reaction temperature. After cooling samples of the vented gases were collected and analysed by gas chromatography. The analytical results demonstrated that the formation of significant quantities of methane had occured by the reaction between anthracene and hydrogen.

'Selectivity' in the Tables herein is defined as the weight fraction of the product quoted in each column to that of the total products.

What we claim is:

1. A process for the production of methane from an organic hydrocarbon containing a plurality of carbon atoms, a process wherein the organic hydrocarbon is contacted in the presence of hydrogen with as the only catalytic entity, a supported ruthenium catalyst, the catalyst prepared by a process comprising the decarbonylation of a ruthenium carbonyl compound.

2. A process as claimed in claim 1 wherein the organic hydrocarbon is an alkane or mixture of alkanes.

3. A process as claimed in claim 1 wherein the organic hydrocarbon comprises alkyl substituted aromatic compounds.

4. A process as claimed in claim 1 wherein the hydrocarbon in vapour form is mixed with hydrogen and an inert gas and the mixture passed over the supported ruthenium catalyst.

5. A process as claimed in any one of the preceding claims wherein the volume proportion of the hydrocarbon to hydrogen contacted with the catalyst is in the range from 1:2 to 1:25.

6. A process as claimed in claim 1 wherein the support material has a particle size in the range from 50 to 300 μm.

7. A process as claimed in any one of claims 1, 2, 3, 4, 5 or 6 wherein the support material is silica.

8. A process as claimed in claim 1 wherein the carbonyl compound is a polynuclear ruthenium carbonyl.

9. A process as claimed in claim 1 wherein each molecule of the carbonyl compound contains a plurality of ruthenium atoms joined by metal-metal bonds.

10. A process as claimed in claim 1 wherein the catalyst is prepared by the deposition of a ruthenium carbonyl compound onto a support material in the absence of moisture followed by decarbonylation of the ruthenium carbonyl compound to metal clusters.

11. A process as claimed in claim 10 wherein the ruthenium carbonyl compound was deposited from solution by evaporation of a solvent from the solution.

12. A process as claimed in claims 10 or 11 wherein the dispersion of deposited carbonyl compound on the surface of the support was rendered homogeneous by applying dry solvent to the supported carbonyl compound and evaporating the solvent whilst the supported compound is stirred.

13. A process as claimed in claim 1 wherein the decarbonylation was conducted by a thermal decomposition of the carbonyl compound.

14. A process as claimed in claim 13 wherein the thermal decomposition of the ruthenium carbonyl compound is conducted by heating the compound on the support to a temperature in the range 100°–500° C. in an atmosphere consisting of a mixture of nitrogen and hydrogen.

15. A process as claimed in claim 14 wherin the heating of the carbonyl compound is performed in two stages, the first stage being in an atmosphere consisting of nitrogen only at a temperature in the range from 100° C. to 200° C. and the second stage being at a higher temperature in an atmosphere containing hydrogen.

16. A process as claimed in claim 15 wherein the atmosphere for the second stage of the heating contains from 10% to 50% by volume of hydrogen in an inert gas.

17. A process as claimed in either claim 15 or claim 16 wherein the second stage of the heating is at temperature in the range 300°–350° C.

* * * * *